(12) United States Patent
Chae et al.

(10) Patent No.: US 8,785,132 B2
(45) Date of Patent: Jul. 22, 2014

(54) APTAMER SANDWICH ASSAYS

(75) Inventors: Young-Chan Chae, Pohang-si (KR); Youn-Dong Kim, Pohang-si (KR); Jung-Hwan Lee, Pohang-si (KR); Ki-Seok Kim, Pohang-si (KR); Dong-Il Han, Pohang-si (KR); Bum-Su Park, Daejeon (KR); Seung-Jin Lee, Pohang-si (KR); Jong-Hun Im, Seoul (KR); Jong-In Kim, Pohang-si (KR); Sung-Ho Ryu, Pohang-si (KR); Sung-Key Jang, Pohang-si (KR)

(73) Assignee: Postech Academy-Industry Foundation, Phang-Shi (KR)

( * ) Notice: Subject to any disclaimer, the term of this patent is extended or adjusted under 35 U.S.C. 154(b) by 357 days.

(21) Appl. No.: 13/092,209

(22) Filed: Apr. 22, 2011

(65) Prior Publication Data

US 2011/0262922 A1    Oct. 27, 2011

Related U.S. Application Data

(60) Provisional application No. 61/327,259, filed on Apr. 23, 2010.

(51) Int. Cl.
*C12Q 1/68* (2006.01)
*G01N 33/53* (2006.01)

(52) U.S. Cl.
CPC .................... *G01N 33/5308* (2013.01)
USPC ........................................ 435/6.12

(58) Field of Classification Search
USPC ................................ 435/91.2, 6.12
See application file for complete search history.

(56) References Cited

U.S. PATENT DOCUMENTS

2010/0267802 A1* 10/2010 Sullenger .................... 514/44 A
2011/0097715 A1*  4/2011 Siret et al. ........................ 435/6

OTHER PUBLICATIONS

Song et al., Trends in analytical Chemistry, vol. 27, No. 2, pp. 108-117, 2008.*
Li et al., Clinical Chemistry, vol. 53, No. 6, pp. 1061-1066, 2007.*
Mir et al., IVD Technology, http://www.ivdtechnology.com, Aptamers Biosensors: an alternative to immunosensors, pp. 1-10, May 2007.*
Kirby et al., Analytical Chemistry, vol. 76, pp. 4066-4075, 2004.*

* cited by examiner

*Primary Examiner* — Cynthia B Wilder
(74) *Attorney, Agent, or Firm* — Lexyoume IP Meister, PLLC

(57) ABSTRACT

The present invention provides methods for identifying the plurality of aptamers that bind to different sites of a target molecule and methods for using the same, for example, in sandwich assays. In particular, the plurality of aptamers binding to different sites of the target molecules is identified from a library of aptamers identified from the same SELEX process.

17 Claims, 10 Drawing Sheets

APTAMER SANDWICH ASSAYS

CROSS REFERENCE TO RELATED APPLICATION

This application claims priority to U.S. Provisional Application No. 61/327,259, filed Apr. 23, 2010, and all the benefits accruing therefrom under 35 U.S.C. §119, which are hereby incorporated by reference for all purposes as if fully set forth herein.

BACKGROUND OF THE INVENTION (a) Field of the Invention

The present invention relates to methods for identifying the plurality of aptamers that bind to different sites of a target molecule and methods for using the same. In particular, the plurality of aptamers binding to different sites of the target molecules is identified from a library of aptamers identified from the same SELEX process.

(b) Description of the Related Art

Aptamers are useful in a wide variety of diagnostic applications including in two site binding assays such as sandwich Enzyme liked immunosorbent assay (ELISA). A sandwich type assay using aptamers requires two different aptamers that recognize different binding site of target molecules. Sandwich type assays are highly specific and sensitive, and therefore are useful as a diagnostic tool and are often used in a wide variety of research and clinical settings. Unfortunately, there is no method for readily identifying two aptamers needed in a sandwich type assay. In fact, most sandwich type assays use only one aptamers, if at all, and an antibody or a protein as a complementary unit for a sandwich type assay. This is mainly due to a difficulty in finding two different aptamers that bind to two different site of a protein or a target biological moiety.

Therefore, there is a need for a method for identifying two different aptamers that are needed in a sandwich type assay.

SUMMARY OF THE INVENTION

Some aspects of the invention provide methods for identifying a pair of target binding aptamer, wherein first target binding aptamer and second target binding aptamer bind to separate non-overlapping sites on the target. Such methods use the same library of aptamers that are selected using a SELEX process. In contrast to the conventional wisdom, the present inventors discovered that certain SELEX processes can include a plurality of aptamers that can bind to different binding sites of a target molecule. The plurality of aptamers that bind to different binding sites of the target molecule can be used in a variety of application including, but not limited to, sandwich assays such as ELISA, fluorescence polarization, surface plasmon resonance, diffractive optics technology, biolayer interferometry, colorimetric resonant reflection, resonant waveguide grating type assay.

DETAILED DESCRIPTION OF THE EMBODIMENTS

Figure 1:
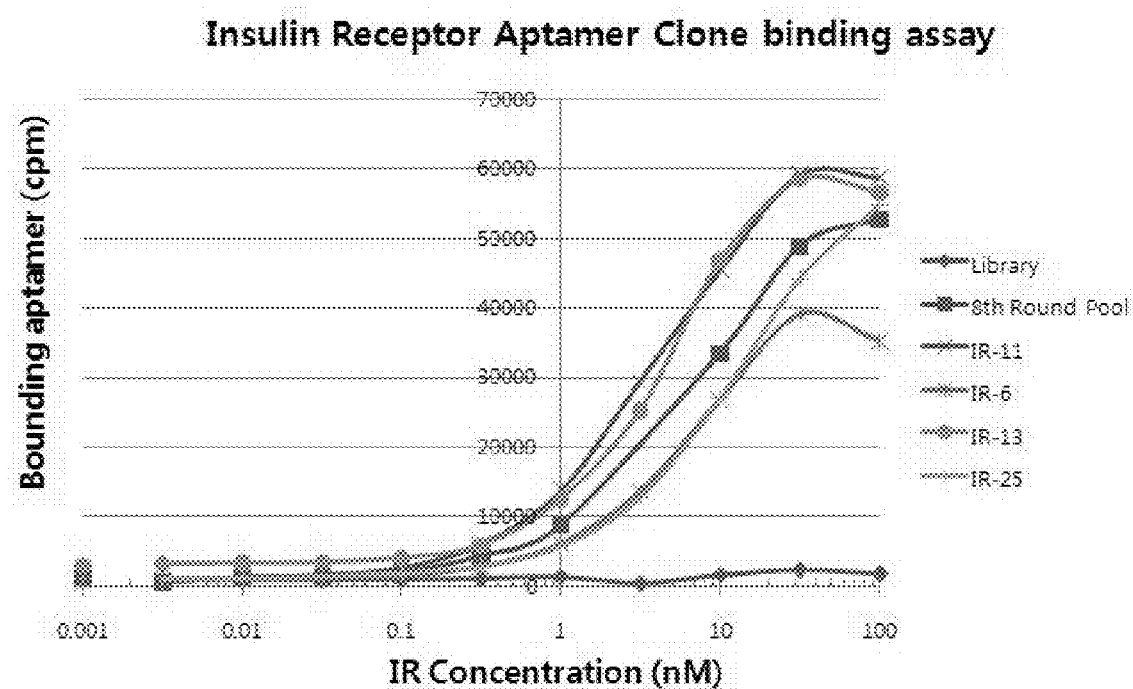
FIG. 1 is a graph showing binding assay results of selected cloned Insulin receptor (IR) binding aptamers. Protein-bound $^{32}$P-aptamers were partitioned from unbound $^{32}$P-aptamers by filtration through nitrocellulose. Data was fit using a biphasic binding equation.

The terms "nucleic acid" "polynucleotide" and "oligonucleotide" are used interchangeable herein and refer to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

The term "detectably labeled" means that an agent (e.g., a probe) has been conjugated with a label that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

Aptamers are oligonucleic acid or peptide molecules that bind to a specific target molecule. Typically, aptamers are DNA or RNA oligonucleotides selected from random-sequence, single-stranded nucleic acid libraries by an in vitro selection and amplification procedure known as SELEX (systematic evolution of ligands by exponential enrichment). For examples of SELEX processes see U.S. Pat. Nos. 5,270,163; 5,475,096; and 5,567,588, which are incorporated herein by reference in their entirety. The selected aptamers are capable of adapting unique tertiary structures and recognizing target molecules with high affinity and specificity. In some instances, binding affinities of aptamers are known to be comparable to those of antibodies. Moreover, aptamers can be modified chemically at defined positions and linked to solid surfaces. In addition, aptamers are easy to screen and can be reproducibly obtained in large quantities and at low cost. Because of these and other advantages, aptamers are useful in research, industrial and clinical applications including, but not limited to, as diagnostic agents.

Because of sensitive, accuracy, and automated high-throughput capability, two site binding assay is one of the most commonly used techniques for a routine analysis of target molecules (e.g., proteins and small molecules) in a variety of fields including clinical, food, and environmental fields. Exemplary two site binding assays include, but are not limited to, ELISA, alphalisa assay, and many other assays known to one skilled in the art. These two site binding assays offer high through put, thereby making it possible to perform a large quantity of analysis within a relatively short period of time.

It is believed that aptamer based two site binding assay can be advantageous compared to an antibody based assay such as ELISA, fluorescence polarization, surface plasmon resonance, diffractive optics technology, biolayer interferometry, colorimetric resonant reflection, and resonant waveguide grating system. One of the major advantages of the aptamer based two site binding assay is not having to produce the necessary antibodies for the assay. While many methods are known for producing the desired antibody, they increase the cost and time for developing such assay systems.

While aptamer based two site binding assay offer a tremendous advantage over antibody based assay systems, currently there are no methods for relatively easily finding two aptamers that interact at different site of the target molecule. Surprisingly and unexpectedly, the present inventors have found that aptamers that bind to different sites of the target molecule can be readily identified from a library of aptamers that are identified from the same SELEX process. It is commonly believed that the SELEX process leads to a library of aptamers that binds to the same binding site of the target molecule. In contrast, however, the present inventors have discovered that one can identify aptamers from the same SELEX process that bind to different sites of the target molecule.

Figure 3:
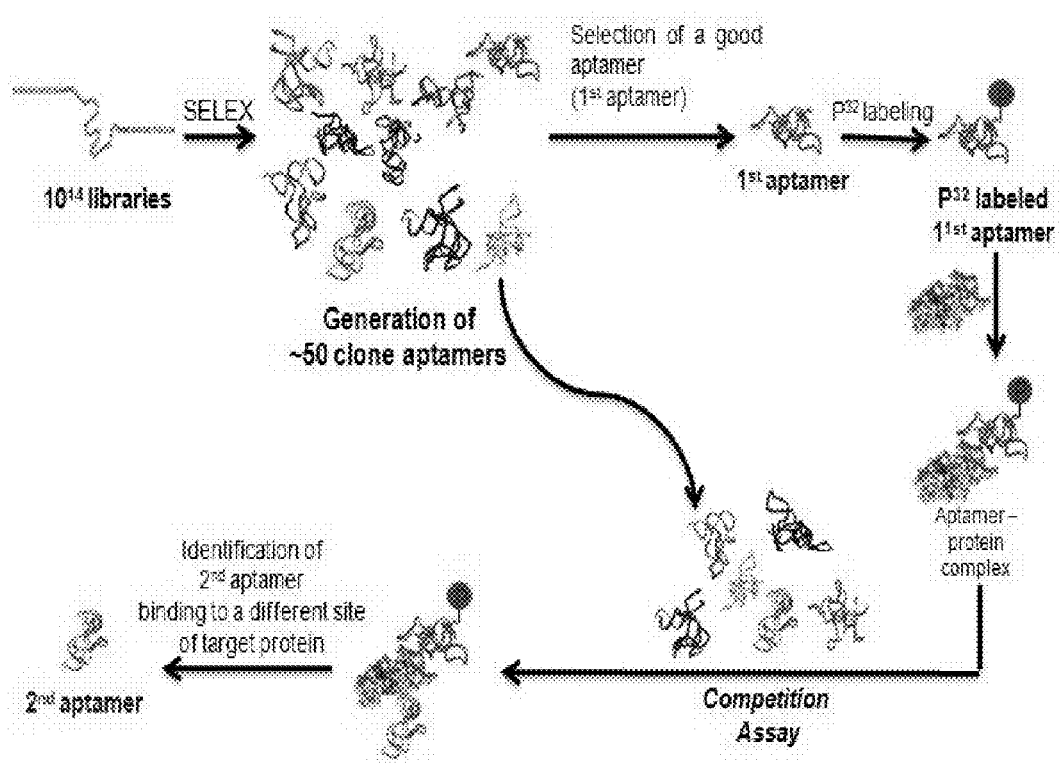
FIG. 3 is a schematic illustration of the competition assay for finding a pair of aptamer that have different binding site to target proteins. After a SELEX process, about 50 aptamers are cloned and amplified. The amplified aptamers are tested for binding affinity. From this binding assay, the $1^{st}$ aptamer is selected and $^{32}$P labeled. The $1^{st}$ aptamer is then incubated with the target protein to produce a $1^{st}$ aptamer-protein complex. Other cloned and amplified, but unlabeled, aptamers are then incubated with the $1^{st}$ aptamer-protein complex. A $2^{nd}$ aptamer that binds to a different area of the target protein is identified.

One aspects of the invention for identifying aptamer pair that bind to different sites of the target molecule is schematically illustrated in FIG. 3. Using this strategy, the present inventors have found aptamers that bind to different sites of the target molecule. A pair of aptamer that is identified using methods of the invention can be used in any of the variety of sandwich assay methods, such as ELISA. Methods of the invention allow identification of an aptamer pair in which each of the aptamer binds to a different site of the target molecule from the same library of aptamers produced by the SELEX process.

As discussed in detail in the EXAMPLES section below, using methods of the invention the present inventors were able to identify and select (from the same library of aptamers produced by the SELEX process) a number of pair of aptamers that bind to different sites of the target molecule. In some instances, the present inventors have found and cloned at least 50 different insulin receptor (i.e., IR) or ERBB2 binding aptamers using methods disclosed herein. As an example, the present inventors identified an aptamer (IR-13; SEQ ID NO: 13) that has a dissociation constant (Kd) of 4.83 nM for IR. Another aptamer (ERBB2-12; SEQ ID NO: 33) was identified that has Kd of 0.78 nM for ERBB2. These aptamers are used as the $1^{st}$ target binding aptamer to identify a second target binding aptamer that binds to the different sites of IR and ERBB2. The second target binding aptamer is identified by a competition method using the $1^{st}$ target binding aptamer that is $P^{32}$ labeled. Using the methods disclosed herein, the present inventors found several aptamers that did not compete with the $1^{st}$ aptamers. In the case of ERBB2 protein, aptamer ERBB2-1 (SEQ ID NO: 27) had dissociation constant of 3.05 nM and was chosen as the second binding aptamer. In the case of IR, aptamer IR-6 (SEQ ID NO: 6) had dissociation constant of 4.6 nM and was selected as the second binding aptamer. When these pairs of aptamers are used in ELISA, the aptamer-based ELISA resulted in detection limit of about 300 pg/mL for IR and about 10 pg/mL for ERBB2. These results show that a SELEX process includes aptamers that bind to different sites of the target molecule.

Some aspects of the invention provide methods for identifying a target binding aptamer pair (e.g., nucleic acid ligands and peptide ligands) of a given target molecule from a candidate mixture of a library of aptamers. Such methods typically comprise:

(a) preparing mixture of aptamers composed of 70-80 mer single stranded oligonucleotides containing 35-45 mer random nucleotide, and fixed nucleotide at both 5' end and 3'-end respectively;

(b) contacting the mixture of aptamers with the target molecule to form aptamer-target complexes, and selecting candidate aptamers among the mixture of aptamers, wherein the candidate aptamers form the aptamer-target complexes;

(c) identifying first target binding aptamer among the candidate aptamers, wherein a dissociation constant (kd) of the first target binding aptamer to the target molecule is 10 nM or less under 35-40° C. and pH 7.0-8.0;

(d) contacting the first target binding aptamer with the target molecule to form first target binding aptamer-target complex;

(e) contacting the first target binding aptamer-target complex with the candidate aptamers to form first target binding aptamer-target-second target binding aptamer complex; and (f) identifying the second target binding aptamer among the candidate aptamers, wherein the second target binding aptamer forms the first target binding aptamer-target-second target binding aptamer complex and a dissociation constant (kd) of the second target binding aptamer to the target molecule is 100 nM or less under 35-40° C. and pH 7.0-8.0.

The first target binding aptamer and the second target binding aptamer bind to separate non-overlapping sites (e.g., different binding sites) on the target molecule.

The mixture of aptamers are composed of 65~85 mer, more preferable, 70~80 mer single stranded oligonucleotides containing 35~45 mer random nucleotide and fixed nucleotide at both 5'-end and 3'-end, respectively.

As used herein, the random nucleotide means a nucleotide fragment with high diversity that is giving chance of suitable structure capable of binding specifically to the target molecule.

Preferably, the fixed nucleotide is composed of 15~25 mer single stranded oligonucleotides at both 5' end and 3'-end, respectively. The oligonucleotide sequence at 5' end is 5'-GAGTGACCGTCTGCCTG-3'(SEQ ID NO: 58), and the oligonucleotide sequence at 3' end is 5'-CAGCCACACCAC-CAGCC-3'(SEQ ID NO: 59).

Therefore, the mixture of aptamers containing 35~45 mer random nucleotides is flanked by fixed regions 5'-GAGT-GACCGTCTGCCTG(SEQ ID NO: 58)-35~45N(SEQ ID NO: 1~57)-CAGCCACACCACCAGCC-3'(SEQ ID NO: 59).

A dissociation constant (kd) of the candidate aptamers to the target molecule is an important factor to consider when selecting the first or second target binding aptamers. Preferably the Kd of the first target binding aptamers to the target molecule is 10 nM or less, more preferable 5 nM or less, under 35-40° C. and pH 7.0-8.0 (in vivo conditions). And preferably the Kd of the second target binding aptamers to the target molecule is 100 nM or less, more preferable 50 nM or less, under 35-40° C. and pH 7.0-8.0.

Meanwhile, quantity of binding aptamers to the target is important factor as well as Kd to consider when selecting the first or second target binding aptamer among the candidate aptamers. The more binding aptamers binds to the target, the better the binding strength is.

In a preferable embodiment, among candidate aptamers, an aptamer having the highest affinity to the target at 35-40° C. and pH 7.0-8.0, that is, the aptamer that shows the greatest aptamer-target binding in terms of its amount under the conditions of 35-40° C. and pH 7.0-8.0, may be selected as the first target binding aptamer. After the selection is made, a second target binding aptamer can be selected among the candidate aptamers, where the second target binding aptamer shows the binding yield (amount) to the target (to which the selected first target binding aptamer has been bound) of 50% or more relative to the binding amount of the first target binding aptamer with the target.

When the Kd of the candidate aptamers to the target molecule is equal or similar, the aptamer having more quantity of binding to the target can be the first or second target binding aptamers.

In one embodiments, the target molecule is insulin receptor (Acc# P06213), and preferably, the random nucleotide sequence of the candidate aptamers are two or more selected from the nucleotide sequence shown in table 1.

TABLE 1

| SEQ ID NO. | nucleotide sequence |
|---|---|
| 1 | AAGGGTAGGCATATATCTCGAGGTCGGAGTAACCGCTTGA |
| 2 | GCATGCTTCTTAGGCCTGATGGCCGACCAGTTTGACGGAA |
| 3 | AGTGATTCAAATTATGACCCCCTTTTAAAGAGCATACAAA |
| 4 | ATTATTAACGAGATGCATCATGCCTGATACCAGACTAAGC |
| 5 | GGTTCGTGACTGAACTCGGTGTGGGTGGCTTGGGTTTGGT |
| 6 | TGGGTACAGTCTTTAGCTTACACAGGCTCCTGAAGACGCA |
| 7 | TTGATTATTAACGAGATGAGCCCCTCCTGACAACCTCAC |
| 8 | TGTATGAGCTGATGCGGTTTCACCGAGCAGACAGACTCCT |
| 9 | AGATCGGTGCCAAGTCTCCCTTTTCTGGTCCGCTGATAGA |
| 10 | TGTGGTGTAACTATTATTAATGAGATGCAGTAGGCCTGAC |
| 11 | TAAGGTTTAAGCTTGGCCTAATGGTGCTATCAGGCTCAG |
| 12 | TGGGTACAGTGTTTAGCTTGCACAGGCTCCTGAAGACACT |
| 13 | TTATCCACTATGGCTTCTCATTCAAATAAGTGCGATCGAT |
| 14 | GCATGCTTCTTAGGACTGATGGCCGACCAGTCTGACGGAA |
| 15 | AGGAACTTGCCCGTTGCTGTTTCATTAGCTGATGCGCTTA |
| 16 | GAATGTCGCCCTTTCTCATTGAAATTATGGCGTGGAGGTA |
| 17 | GTCGCCTGATGGCGGTGGCTTTATGCTTTAAAGTCACGGG |
| 18 | GCCTGACCTCATTCACGCACTGTTGGGCAGACTATGAATT |
| 19 | GGTCGTGACTGAACTCGGTGTGGGTGGCTTGGGTTTGTT |
| 20 | AAAGCAGTGCATGGCTATTTATTAAGAAAGACGGGAGTTT |
| 21 | AGTTGCCGCCGTCTTCATTGAACTGTACTAGGTGCCCTC |
| 22 | ATAAACCATTCCGTGGCTGGCTGACCTCTTTCACGCGATC |
| 23 | TGTGATTCAAATTATGGCCCCCTTTTAAAGAGCATACAAA |
| 24 | GGACTCTTACGCGGTTAACCCTCATGGTTTTGTGAGTCTG |
| 25 | AGATCCGACTGTTTACTGTTTAACAGCCGGCTGATGGACC |
| 26 | TGTATAATTGGGTTCTTGAAATTACCCCGAAGCTAGGTCA |

Preferably, the random nucleotide sequence of the First target binding aptamer among the nucleotide sequences shown in table 1 is SEQ ID NOS: 6, 11, 13, or 25, and more preferably, SEQ ID NO: 13.

For example, when the random nucleotide sequence of the First target binding aptamer is SEQ ID NO: 13, the random nucleotide sequence of the second target binding aptamer may be SEQ ID NOS: 6, 9, 12, 18 or 22, and more preferably, SEQ ID NO: 6.

In other embodiments, the target molecule is ERBB2 (Human Epidermal growth factor Receptor 2 (Human), Acc# P04626), and the random nucleotide sequence of the candidate aptamers are two or more selected from the nucleotide sequence shown in table 2.

TABLE 2

| SEQ ID NO. | nucleotide sequence |
|---|---|
| 27 | ATGTTAGAGTTTGCCTGAGTGCCTCGTAAGGGCGTAACAA |
| 28 | TACTGGGCCCGTTAGCCTCTGGCGCTCCTTCGCTTGTGCC |
| 29 | TTATCAACGCACTGAGGGCGTCAGCTTCTTTTTAGG |
| 30 | ATGTAGAGTTTGCCTGAGTGCCTCGCAAGGGCGTAACAG |
| 31 | TCCTGTCCCGGTTTACACAAGTTAAGGCAGCCGCTGGATA |
| 32 | GTCTGAACACCGAGATTAGCTGAACGAACGGTATGGACGT |
| 33 | TCCTGGCATGTTCGATGGAGGCCTTTGATTACAGCCCAGA |
| 34 | CGCGATTAGATGAACGCACAATACCCGTTCTGAGTAAAGT |
| 35 | GTCTGAACACCGAGATTAGCCGAACGAACGGTATGGACGT |
| 36 | GTTAGACTGAACGCACTGAGGGCCGCAGCCTATCTGAAGG |
| 37 | ATGTTAGAGTTTGCCTGAGTGCCTCGCAAGGGCGTAACAA |
| 38 | GTCTGAGCATCGCGTTTAGCCGAACGCTCGGTGAGGTAGAT |
| 39 | TCATGGCATGTTCGATGGAGGCCTTTGATTACAGCCCAGA |
| 40 | CTACACGAATCAACTCCCCTCCGCATACTGAACATCACAA |
| 41 | TTAGCAAAATGCCATGTGCGTCCTGTCCCGGTTTACAGC |
| 42 | TGATGTCCCCAACTCAGCTGTGAATCTATGCCCCCGCCCA |
| 43 | CTGAGCGGTTACTACACCACCGTGAGACCTTAGTTACAAA |
| 44 | ATTAGATGAAAGCGCATTCCAACAACAGATAATCTGAGGG |
| 45 | TTTGGAGTGTCTTACGGTTGGAGTAATCGAGGATGGATGA |
| 46 | CCGTTACCTACCTCCTCGACCGTGGGTGCCCTTAGTCCCA |
| 47 | TCCTGGCATGTTCGATGGAGGCCTTTGATTACAGCCAGA |
| 48 | CCGTTACCTACCTCCTCGACCGTGGGTGCCTTTAGTCCCA |
| 49 | TCCTGGCATGTTCGATGGAGGCCTTTGATTACAGCCCAGT |
| 50 | ATTAGATGAAAGCACATTCCAACAACAGATAATCTGAGGG |
| 51 | ATGTTAGAGTTTGCCTGAGTGCGTCGCAAGGGCGTAACAG |
| 52 | TGAGAAGGGCTGTGCCTTACTCAAAATTTGGGATCTGAA |
| 53 | TCCTGGTATGTTCGATGGAGGCCTTTGATTACAGCCCAGA |
| 54 | TAGATCTCTGATTAGGTAGAACGCCCTACTCTAACGGCAG |
| 55 | TGAGAAGGGCTGTGCCTTACTCAAAATTTGGGGATCTGAA |
| 56 | CGTCCTTGGTGAGTTTGGGTCTGAGCAGGAGCACGTGAGT |
| 57 | ATGTTAGAGTCTGCCTGAGTGCCTCGCAAGGGCGTAACAG |

Preferably, the random nucleotide sequence of the First target binding aptamer among the nucleotide sequences shown in table 2 is SEQ ID NOS: 27, 33, 36, or 44, and more preferably, SEQ ID NO: 33.

When the random nucleotide sequence of the First target binding aptamer is SEQ ID NO:33, the random nucleotide sequence of the second target binding aptamer is SEQ ID NOS: 27, 31, or 38, and more preferably, SEQ ID NO: 27.

The fixed nucleotide sequence at both 5'-end and 3'-end may be 5'-GAGTGACCGTCTGCCTG-3'(5'-end) (SEQ ID NO: 58) and 5'-CAGCCACACCACCAGCC-3'(3'-end) (SEQ ID NO: 59).

The first target binding aptamer may be labeled with a first label prior to forming the first target binding aptamer-target complex. Any labels that conventionally used for aptamer labeling, and suitable labels may include, but not be limited to, radioisotopes, optical label (e.g., fluorophores and chromophores), mass labels, electron dense particles, magnetic particles, spin labels, molecules that emit chemiluminescence, electrochemically active molecules, enzymes, cofactors, enzyme substrates, and the like. In some embodiments, the first label may comprise an optical label, a radio label, an isotope label, or a combination thereof. In one particular embodiment, the optical label may comprise a fluorophore.

In order to facilitate the identification and/or detection of the binding aptamers, the relatively higher affinity aptamers (candidate aptamers) are often amplified or cloned prior to identifying first target binding aptamer. Such amplification can be achieved by any of the methods known to one skilled in the art including, but not limited to, polymerase chain reaction (i.e., PCR).

In the case where the aptamer is an oligonucleotide, the step (b) can be performed by the method comprising:
(i) performing a first primer extension of the mixture of aptamers with a nucleic acid polymerase to form aptamer pool I;
(ii) removing the target molecule;
(iii) performing a second primer extension of the first primer extension product with a nucleic acid polymerase under conditions suitable for priming the candidate aptamers and forming aptamer pool II; and
(iv) partitioning the aptamer pool II from the remainder of the mixture of aptamers.

Typically, the condition for performing the second primer extension is different from the condition for performing the first primer extension. In this manner, the second primer extension can be performed selectively. Suitable nucleic acid polymerases for primer extension are well known to one skilled in the art and include, but are not limited to, DNA polymerases, RNA polymerases, reverse transcriptase, and Qβ-replicase.

In some embodiments, the two primer extension processes produce nucleic acids of different lengths to allow separation of the higher affinity nucleic acids (candidate aptamers) from the remainder of the mixture of aptamers. It should be appreciated that either the higher affinity nucleic acids or the remainder of the mixture can be chain extended to produce different nucleic acid length aptamers. In one particular embodiment, the first primer extension is performed in the presence of chain terminating nucleotides, i.e., dideoxynucleotides (ddNTP's) and the second primer extension is performed in the absence of chain terminating nucleotides such that only the primer extension product from the higher affinity oligonucleotide is amplifiable by a polymerase chain reaction.

Methods of the invention can be used to develop diagnostic assays, research tools, clinical applications, as well as other applications that use a sandwich type assay method. Methods of the invention can be used to develop a pair of aptamers that can bind to different sites of the same target molecule. By repeating the processes described above, one can also identify and develop assays that utilize a plurality (e.g., three, four, or more) of aptamers. Such systems are useful in increasing the selectivity and/or sensitivity of the assay. A wide variety of target molecules are suitable for methods of the invention. Exemplary target molecules include, proteins (including enzymes and receptors), small molecules (such as drug candidates, drug metabolites, etc.), saccharides, oligosaccharides, oligonucleotides (including RNAs and DNAs), phospholipid, glycolipid, sterol, glycerolipids, carbohydrates (including sugar), vitamins, hormones, neurotransmitters, metabolites and any molecules or chemicals that can be detected using a sandwich type assay.

In other aspects of the invention, methods for detecting the presence of a target molecule in a sample are provided. Such methods may comprise:

(a) contacting the sample with the first target binding aptamer under conditions suitable for producing a first target binding aptamer-target complex;

(b) contacting at least a portion of the first target binding aptamer-target complex with the second target binding aptamer under conditions suitable for producing a first target binding aptamer-target-second target binding aptamer complex; and (c) determining the presence and/or quantity of a target molecule in a sample, by detecting the first target binding aptamer-target-second target binding aptamer complex.

The first and the second target binding aptamers are produced by the methods for identifying a pair of target binding aptamer described herein.

In some embodiments, the target molecule is a protein. Within these embodiments, in some instances the target molecule is insulin receptor, ERBB2, or a combination thereof.

The sample for testing can be any material that potentially contains the target molecule. For example, the sample can be a biological fluid, a tissue, a cell, a cloth, a swab of sample, etc derived from mammals, yeasts, virus, or prokaryotic cells. In some instances, the biological fluid comprises blood, plasma, serum, sputum, urine, semen, cerebrospinal fluid, bronchial aspirate, macerated tissue, rheumatoid arthritis fluid, or a mixture thereof.

In order to facilitate detection, in some embodiments, the first and/or the second target binding aptamer can include a detection system or a label. Suitable detection systems include labels disclosed herein including a fluorophore, radio isotope, enzyme, fluorescence polarization, surface plasmon resonance, diffractive optics technology, biolayer interferometry, colorimetric resonant reflection, resonant waveguide grating, or a combination thereof. Exemplary fluorophores include fluorescein, rhodamine, texas red, eosin, Alexa, cyanine, coumarin, CF dyes, fluoprobes, dylight fluors, oyster dyes, Atto dyes, Hilight Fluores, and others known to one skilled in the art.

The suitable conditions in step (a) and (b) mean conditions that allow aptamers to be active structure such as pH of 7.0-8.0 and 1-10 mM of $MgCl_2$ at Room temperature.

The presence of the target molecule can be detected by separating at least a portion of the first target binding aptamer-target complex prior to step (b). But, for further detecting the quantity of the target molecule in a sample, steps (b) and (c) are needed.

In step (b), at least a portion of the first target binding aptamer-target complex is the region containing the binding site of the second target binding aptamer on the target molecule, except the binding site of the first target binding aptamer.

In some instances, the first target binding aptamer is immobilized on a solid substrate. Such a solid substrate bound aptamer allows analysis on a solid substrate. The solid substrate may include, but not be limited to, a microsphere particle, glass, a silicon wafer, a membrane, a metal, a polymer, or a combination thereof. As disclosed herein, the first target binding aptamer and the second target binding aptamer bind to different and non-overlapping sites on the target molecule.

As a matter of convenience, the detecting method of this invention can be provided in the form of a detecting kit.

The detecting kit comprises the first target binding aptamer as a capture reagent, and the second target binding aptamer as a detection reagent. The first and the second target binding aptamers are defined hereinabove.

The second target binding aptamer may be labeled, and the first target binding aptamer is unlabeled. The preferable labels are defined hereinabove.

Preferably, the kit further comprises a solid substrate for immobilizing the capture reagents, which can be provided separately from the capture reagent, or on which the capture reagents are already immobilized. In consequence, the first target binding aptamer in the kit may be immobilized on a solid substrate, or they may be immobilized on such substrate that is included with the kit or provided separately from the kit.

The kit may further comprise a detection means for the detectable label that is attached to the second target binding aptamer. Also the kit additionally contains other additives such as stabilizers, washing and incubation buffers, and the like.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

The present invention is further explained in more detail with reference to the following examples. These examples, however, should not be interpreted as limiting the scope of the present invention in any manner.

EXAMPLES

Example 1

SELEX with Insulin Receptor Proteins and ERBB2 Proteins 1.1 SELEX Process

The IR and ERBB2 receptor proteins were used as the target proteins for in vitro selection of aptamers from a pool of oligonucleotides (i.e., oligonucleotide library). The oligonucleotide library was composed of 70~80-mer single stranded oligonucleotides containing 35~45-mer random nucleotide regions of IR and ERBB2, and 17-mer fixed nucleotide regions at both 5' end and 3'-end respectively. Specifically a synthetic oligonucleotide template containing 35~45 random nucleotides flanked by fixed regions 5'-GAGTGAC-CGTCTGCCTG(SEQ ID NO: 58)-35~45N-CAGCCACAC-CACCAGCC-3'(SEQ ID NO: 59) complementary to the primers 5'-GAGTGACCGTCTGCCTG-3'(SEQ ID NO: 58) and 5'-BB-GGCTGGTGGTGTGGCTG-3'(SEQ ID NO: 60), where BB denotes three biotin phosphoramidite couplings. This oligonucleotide library was used to identify aptamers with a relatively high binding affinity to IR or ERBB2 under simulated in vivo conditions, e.g., at 37° C. and at pH 7.4. A library of about $1 \times 10^{14}$ aptamers was incubated for 30 min with IR(RnD Systems, Cat#1544-IR) and ERBB2 (RnD Systems, Cat#1129-ER) that were bound to magnetic beads.

The protein-bound aptamers were then partitioned by magnetic separation, and amplified with forward primer (5'-GAGTGACCGTCTGCCTG-3') (SEQ ID NO: 58) and biotinylated reverse primer (5'-BB-GGCTGGTGGTGTGGCTG-3') (SEQ ID NO: 60) and quantitated by real-time PCR.

Twenty-five thermal cycles were conducted at 93° C. for 30 sec, 52° C. for 20 sec, and 72° C. for 60 sec. The resulting double stranded oligonucleotides of PCR amplification were incubated with Streptavidin (Invitrogen, CaT#650-02) bead and the nonbiotinylated single-stranded oligonucleotides were then separated from streptavidin bead-double stranded oligonucleotide complexes by denaturing with 20 mM solution of NaOH.

The resulting bead bound single strand oligonucleotides were then used as templates for primer extension, generating a new pool of aptamers for IR or ERBB2.

The resulting mixture was neutralized with 80 mM of HCl solution. The SELEX process was performed at 37° C. Briefly, 1 mmol aptamer library was dissolved in a buffer solution (40 mM HEPES/pH 7.5, 120 mM NaCl, 5 mM KCl, 5 mM MgCl$_2$, 0.002% tween-20) and heated at 95° C. for 3 min. The mixture was slowly cooled to 37° C. at 0.1° C./sec for aptamer re-folding. To the resulting solution was added 0.1% BSA (Sigma, Cat# A6909), 10 mM of Prothrombin (Enzymersearch, Cat# HP1002), and 10 mM of casein (Fluka, Cat# A2427) to eliminate non-specific aptamer.

The aptamer library was pre-incubated with His-tagged magnetic beads (Invitrogen) to eliminate non-specifically bound aptamer using the magnetic bead. Aptamers in the supernatant were incubated with 10 μmol of purified proteins for 30 min. The target proteins were than captured with His-tagged bead and separated using a magnetic field. The resulting complex was washed three times with a buffer. Aptamers bound to the target proteins were eluted with 2 mM of NaOH solution and amplified via PCR with forward primer (5'-GAGTGACCGTCTGCCTG-3') (SEQ ID NO: 58) and biotinylated reverse primer (5'-BB-GGCTGGTGGTGTGGCTG-3') (SEQ ID NO: 60) The non-biotinylated single-stranded oligonucleotides were separated from streptavidin bead-double stranded oligonucleotide complex using a 20 mM solution of NaOH. The resulting NaOH solution was neutralized with a 80 mM HCl solution and was used in the subsequent SELEX process.

1.2. Cloning and Sequencing

Aptamer pools were amplified using 5'-primer (5'-GAGTGACCGTCTGCCTG-3') (SEQ ID NO: 58) and 3'-primer (5'-GGCTGGTGGTGTGGCTG-3') (SEQ ID NO: 60), and cloned into pUC9 plasmid (Solgent, Cat# SOT01-K020). Sixty individual plasmids were sequenced using DYEnamic ET-terminator cycle sequencing premix kit (Amersham Pharmacia Biotech, Inc., Piscataway, N.J.) and ABI Prism 377 sequencer.

The entire cycle may be repeated for higher precision. Each round of amplification give rise to variants which are different from the previous cycles and thus increasing the diversity of aptamers. 6-20 cycles can be performed for proper selection of aptamers and then the selected sequences are cloned into the vector and sequencing is done.

Eight rounds of iterative selection and amplification were performed in this experiment, and quantitated resulting in a pool of aptamers including, but not limited to, aptamers listed in Table 3 and Table 4.

TABLE 3 random sequences of Insulin Receptor aptamer

| SEQ ID NO. | name | random sequence |
| --- | --- | --- |
| 1 | IR-1 | AAGGGTAGGCATATATCTCGAGGTCGGAGTAACCGCTTGA |
| 2 | IR-2 | GCATGCTTCTTAGGCCTGATGGCCGACCAGTTTGACGGAA |
| 3 | IR-3 | AGTGATTCAAATTATGACCCCCTTTTAAAGAGCATACAAA |
| 4 | IR-4 | ATTATTAACGAGATGCATCATGCCTGATACCAGACTAAGC |
| 5 | IR-5 | GGTTCGTGACTGAACTCGGTGTGGGTGGCTTGGGTTTGGT |
| 6 | IR-6 | TGGGTACAGTCTTTAGCTTACACAGGCTCCTGAAGACGCA |
| 7 | IR-7 | TTGATTATTAACGAGATGAGCCCCTCCTGACAACCTCAC |
| 8 | IR-8 | TGTATGAGCTGATGCGGTTTCACCGAGCAGACAGACTCCT |
| 9 | IR-9 | AGATCGGTGCCAAGTCTCCCTTTTCTGGTCCGCTGATAGA |
| 10 | IR-10 | TGTGGTGTAACTATTATTAATGAGATGCAGTAGGCCTGAC |
| 11 | IR-11 | TAAGGTTTAAGCTTGGCCTAATGGTGCTATCAGGCTCAG |
| 12 | IR-12 | TGGGTACAGTGTTTAGCTTGCACAGGCTCCTGAAGACACT |
| 13 | IR-13 | TTATCCACTATGGCTTCTCATTCAAATAAGTGCGATCGAT |
| 14 | IR-14 | GCATGCTTCTTAGGACTGATGGCCGACCAGTCTGACGGAA |
| 15 | IR-15 | AGGAACTTGCCCGTTGCTGTTTCATTAGCTGATGCGCTTA |
| 16 | IR-16 | GAATGTCGCCCTTTCTCATTGAAATTATGGCGTGGAGGTA |
| 17 | IR-17 | GTCGCCTGATGGCGGTGGCTTTATGCTTTAAAGTCACGGG |
| 18 | IR-18 | GCCTGACCTCATTCACGCACTGTTGGGCAGACTATGAATT |
| 19 | IR-19 | GGTCGTGACTGAACTCGGTGTGGGTGGCTTGGGTTTGTT |
| 20 | IR-20 | AAAGCAGTGCATGGCTATTTATTAAGAAAGACGGGAGTTT |
| 21 | IR-21 | AGTTGCCGCCGTCTTCATTGAACTGTACTAGGTGCCCTC |
| 22 | IR-22 | ATAAACCATTCCGTGGCTGGCTGACCTCTTTCACGCGATC |
| 23 | IR-23 | TGTGATTCAAATTATGGCCCCCTTTTAAAGAGCATACAAA |
| 24 | IR-24 | GGACTCTTACGCGGTTAACCCTCATGGTTTTGTGAGTCTG |
| 25 | IR-25 | AGATCCGACTGTTTACTGTTTAACAGCCGGCTGATGGACC |
| 26 | IR-26 | TGTATAATTGGGTTCTTGAAATTACCCCGAAGCTAGGTCA |

TABLE 4 random sequences of ERBB2 aptamer

| SEQ ID NO. | Name | random sequence |
| --- | --- | --- |
| 27 | ERBB2-1 | ATGTTAGAGTTTGCCTGAGTGCCTCGTAAGGGCGTAACAA |
| 28 | ERBB2-2 | TACTGGGCCCGTTAGCCTCTGGCGCTCCTTCGCTTGTGCC |

TABLE 4-continued random sequences of ERBB2 aptamer

| SEQ ID NO. | Name | random sequence |
|---|---|---|
| 29 | ERBB2-3 | TTATCAACGCACTGAGGGCGTCAGCTTCTTTTTAGG |
| 30 | ERBB2-4 | ATGTAGAGTTTGCCTGAGTGCCTCGCAAGGGCGTAACAG |
| 31 | ERBB2-5 | TCCTGTCCCGGTTTACACAAGTTAAGGCAGCCGCTGGATA |
| 32 | ERBB2-6 | GTCTGAACACCGAGATTAGCTGAACGAACGGTATGGACGT |
| 33 | ERBB2-7 | TCCTGGCATGTTCGATGGAGGCCTTTGATTACAGCCCAGA |
| 34 | ERBB2-8 | CGCGATTAGATGAACGCACAATACCCGTTCTGAGTAAAGT |
| 35 | ERBB2-9 | GTCTGAACACCGAGATTAGCCGAACGAACGGTATGGACGT |
| 36 | ERBB2-10 | GTTAGACTGAACGCACTGAGGGCCGCAGCCTATCTGAAGG |
| 37 | ERBB2-11 | ATGTTAGAGTTTGCCTGAGTGCCTCGCAAGGGCGTAACAA |
| 33 | ERBB2-12 | TCCTGGCATGTTCGATGGAGGCCTTTGATTACAGCCCAGA |
| 38 | ERBB2-13 | GTCTGAGCATCGCGTTTAGCCGAACGCTCGGTGAGGTAGAT |
| 39 | ERBB2-14 | TCATGGCATGTTCGATGGAGGCCTTTGATTACAGCCCAGA |
| 40 | ERBB2-15 | CTACACGAATCAACTCCCCTCCGCATACTGAACATCACAA |
| 41 | ERBB2-16 | TTAGCAAAATGCCATGTGCGTCCTGTCCCGGTTTACAGC |
| 42 | ERBB2-17 | TGATGTCCCCAACTCAGCTGTGAATCTATGCCCCCGCCCA |
| 43 | ERBB2-18 | CTGAGCGGTTACTACACCACCGTGAGACCTTAGTTACAAA |
| 44 | ERBB2-19 | ATTAGATGAAAGCGCATTCCAACAACAGATAATCTGAGGG |
| 33 | ERBB2-20 | TCCTGGCATGTTCGATGGAGGCCTTTGATTACAGCCCAGA |
| 45 | ERBB2-21 | TTTGGAGTGTCTTACGGTTGGAGTAATCGAGGATGGATGA |
| 46 | ERBB2-22 | CCGTTACCTACCTCCTCGACCGTGGGTGCCCTTAGTCCCA |
| 47 | ERBB2-23 | TCCTGGCATGTTCGATGGAGGCCTTTGATTACAGCCAGA |
| 48 | ERBB2-24 | CCGTTACCTACCTCCTCGACCGTGGGTGCCTTTAGTCCCA |
| 37 | ERBB2-25 | ATGTTAGAGTTTGCCTGAGTGCCTCGCAAGGGCGTAACAA |
| 49 | ERBB2-26 | TCCTGGCATGTTCGATGGAGGCCTTTGATTACAGCCCAGT |
| 46 | ERBB2-27 | CCGTTACCTACCTCCTCGACCGTGGGTGCCCTTAGTCCCA |
| 50 | ERBB2-28 | ATTAGATGAAAGCACATTCCAACAACAGATAATCTGAGGG |
| 33 | ERBB2-29 | TCCTGGCATGTTCGATGGAGGCCTTTGATTACAGCCCAGA |
| 51 | ERBB2-30 | ATGTTAGAGTTTGCCTGAGTGCGTCGCAAGGGCGTAACAG |
| 52 | ERBB2-31 | TGAGAAGGGCTGTGCCTTACTCAAAATTTGGGATCTGAA |
| 36 | ERBB2-32 | GTTAGACTGAACGCACTGAGGGCCGCAGCCTATCTGAAGG |
| 35 | ERBB2-33 | GTCTGAACACCGAGATTAGCCGAACGAACGGTATGGACGT |
| 35 | ERBB2-34 | GTCTGAACACCGAGATTAGCCGAACGAACGGTATGGACGT |
| 35 | ERBB2-35 | GTCTGAACACCGAGATTAGCCGAACGAACGGTATGGACGT |
| 53 | ERBB2-36 | TCCTGGTATGTTCGATGGAGGCCTTTGATTACAGCCCAGA |
| 54 | ERBB2-37 | TAGATCTCTGATTAGGTAGAACGCCCTACTCTAACGGCAG |
| 55 | ERBB2-38 | TGAGAAGGGCTGTGCCTTACTCAAAATTTGGGGATCTGAA |
| 55 | ERBB2-39 | TGAGAAGGGCTGTGCCTTACTCAAAATTTGGGGATCTGAA |
| 44 | ERBB2-40 | ATTAGATGAAAGCGCATTCCAACAACAGATAATCTGAGGG |

TABLE 4-continued random sequences of ERBB2 aptamer

| SEQ ID NO. | Name | random sequence |
|---|---|---|
| 35 | ERBB2-41 | GTCTGAACACCGAGATTAGCCGAACGAACGGTATGGACGT |
| 56 | ERBB2-42 | CGTCCTTGGTGAGTTTGGGTCTGAGCAGGAGCACGTGAGT |
| 33 | ERBB2-43 | TCCTGGCATGTTCGATGGAGGCCTTTGATTACAGCCCAGA |
| 35 | ERBB2-44 | GTCTGAACACCGAGATTAGCCGAACGAACGGTATGGACGT |
| 50 | ERBB2-45 | ATTAGATGAAAGCACATTCCAACAACAGATAATCTGAGGG |
| 33 | ERBB2-46 | TCCTGGCATGTTCGATGGAGGCCTTTGATTACAGCCCAGA |
| 50 | ERBB2-47 | ATTAGATGAAAGCACATTCCAACAACAGATAATCTGAGGG |
| 36 | ERBB2-48 | GTTAGACTGAACGCACTGAGGGCCGCAGCCTATCTGAAGG |
| 33 | ERBB2-49 | TCCTGGCATGTTCGATGGAGGCCTTTGATTACAGCCCAGA |
| 57 | ERBB2-50 | ATGTTAGAGTCTGCCTGAGTGCCTCGCAAGGGCGTAACAG |

Example 2

Identification of First Target Binding Aptamer

Aptamers identified using the above SELEX process were amplified by PCR and cloned as described above. Up to fifty randomly picked plasmid clones were sequenced. Several aptamers identified after eight rounds of SELEX process had sequences shown in Table 3 and Table 4. To verify that cloned aptamers bind to IR or ERBB2, aptamers that had same sequence in the aptamer pool were tested for binding affinity. Briefly, aptamers were incubated with various concentrations of target His-tagged proteins and the target His-tagged proteins were captured on Talon bead. Radio labeled aptamers that were bound to target proteins were then detected by phosphoimager.

Specifically, Aptamer-protein equilibrium dissociation constants (Kd's) were determined by the nitrocellulose-filter binding method as described by White et al. in *Mol. Ther.*, 2001, 4(6), 567-73. For all binding assays, aptamers were dephosphorylated using alkaline phosphatase (New England Biolab) and labeled at the 5'-end using T4 polynucleotide kinase (New England Biolabs, Beverly, Mass.) and $[\gamma^{32}P]$ ATP (Amersham Pharmacia Biotech, Piscataway, N.J.) as described by Fitzwater et al., in *Methods Enzymol*, 1996, 267, 275-301. Briefly, prior to subjecting to a binding assay, the aptamer was heated to 95° C. for 3 min, and then slowly cooled to 37° C. at 0.1° C./sec in a buffer solution (40 mM HEPES/pH 7.5, 120 mM NaCl, 5 mM KCl, 5 mM $MgCl_2$, and 0.002% tween-20) to allow aptamer refolding. Direct binding assays were carried out by incubating the $^{32}P$-labeled aptamers at a concentration of less than 10 pM and the protein at concentrations ranging from 1 mM to 10 fM in a buffer solution at 37° C. The fraction of bound aptamer was quantified with a PhosphorImager (Fuji FLA-5100 Image Analyzer, Tokyo, Japan). Raw binding data were corrected for nonspecific background binding of the radio-labeled aptamer to the nitrocellulose filter as described by White et al., in *Mol. Ther.*, 2001, 4(6), 567-73 and reported as the mean±standard error of the mean (SEM) of three experiments.

Figure 2:
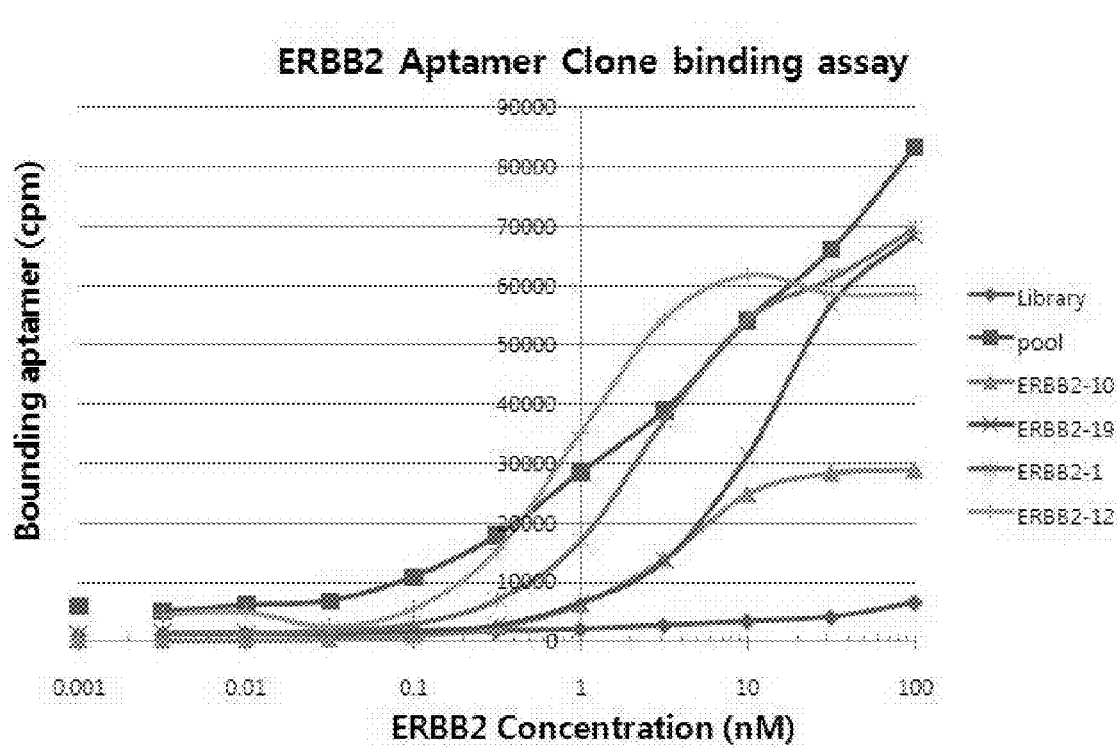
FIG. 2 is a graph showing binding assay results of selected cloned ERBB2 binding aptamers. Protein-bound $^{32}$P-aptamers were partitioned from unbound $^{32}$P-aptamers by filtration through nitrocellulose. Data was fit using a biphasic binding equation.

The results showed that IR-13 aptamer (SEQ ID NO: 13) had Kd of about 4.83 nM and ERBB2-12 (SEQ ID NO: 33) aptamer had Kd of about 0.78 nM. However, there was no significant amount of non-specific binding to a library mixture of aptamers. See FIGS. 1, 2 and Table 5, 6.

TABLE 5

Kd of IR binding aptamers

| Aptamers | Kd (nM) |
|---|---|
| Library | >1000 |
| 8$^{th}$ Round Pool | 12.41 + 4.34 |
| IR-11 | 5.48 + 0.26 |
| IR-6 | 4.60 + 1.08 |
| IR-13 | 4.83 + 0.78 |
| IR-25 | 13.31 + 0.28 |

TABLE 6

Kd of ERBB2 binding aptamers

| Aptamers | Kd (nM) |
|---|---|
| Library | >1000 |
| 8$^{th}$ Round Pool | 3.36 ± 0.80 |
| ERBB2-10 | 3.70 ± 0.39 |
| ERBB2-19 | 15.79 ± 1.25 |
| ERBB2-1 | 3.05 ± 0.20 |
| ERBB2-12 | 0.78 ± 0.12 |

These results showed that IR-13 and ERBB2-12 aptamers specifically interact with each target proteins, and therefore IR-13 and ERBB2-12 aptamers were selected as the 1$^{st}$ target binding aptamers for a respective sandwich assay.

Meanwhile, in table 5 the results showed that IR-6 aptamer (SEQ ID NO: 6) had the Kd of about 4.60 nM, less than the Kd of IR-13 aptamer (4.83 nM), but absolute quantity of binding aptamers to the target is important factor as well as Kd to consider when selecting the first target binding aptamer. Therefore the IR-13 aptamer, had the similar Kd with IR-6, and much more quantity of binding aptamers to the target than the IR-6, is selected for the 1$^{st}$ target binding aptamers.

Example 3

Identification of 2$^{nd}$ Target Binding Aptamers

To identify aptamers that bind to a different site of the target protein compared to the 1$^{st}$ target binding aptamers identified above, a selection method using a competition assay was used. See the schematic illustration in FIG. 3.

Aptamers were labeled and allowed to refold as described above. See 'example 2' above. The $^{32}$P-labeled 1$^{st}$ target binding aptamer at a concentration of about 2 nM was preincubated with 10 nM of the target protein for 15 min at 37° C. to produce a labeled aptamer-protein complex (i.e., first target binding aptamer-protein complex). The resulting complex was incubated with other aptamers (at a concentration of about 30 nM) that were not labeled. It was expected that if the second aptamer shares the same binding site on the target protein with the 1$^{st}$ binding aptamer, there would be competitive binding between the labeled 1$^{st}$ target binding aptamer and the second target binding aptamer. If not, one would not expect to see any radio isotope signal of the free 1$^{st}$ target binding aptamer. The fraction of bound $^{32}$P-labeled aptamer was quantified with a PhosphorImager (Fuji FLA-5100 Image Analyzer, Tokyo, Japan). Raw binding data were corrected for nonspecific background binding of radio-labeled aptamer to the nitrocellulose filter and reported as the mean±standard error of the mean (SEM) of three experiments.

Figure 4A:
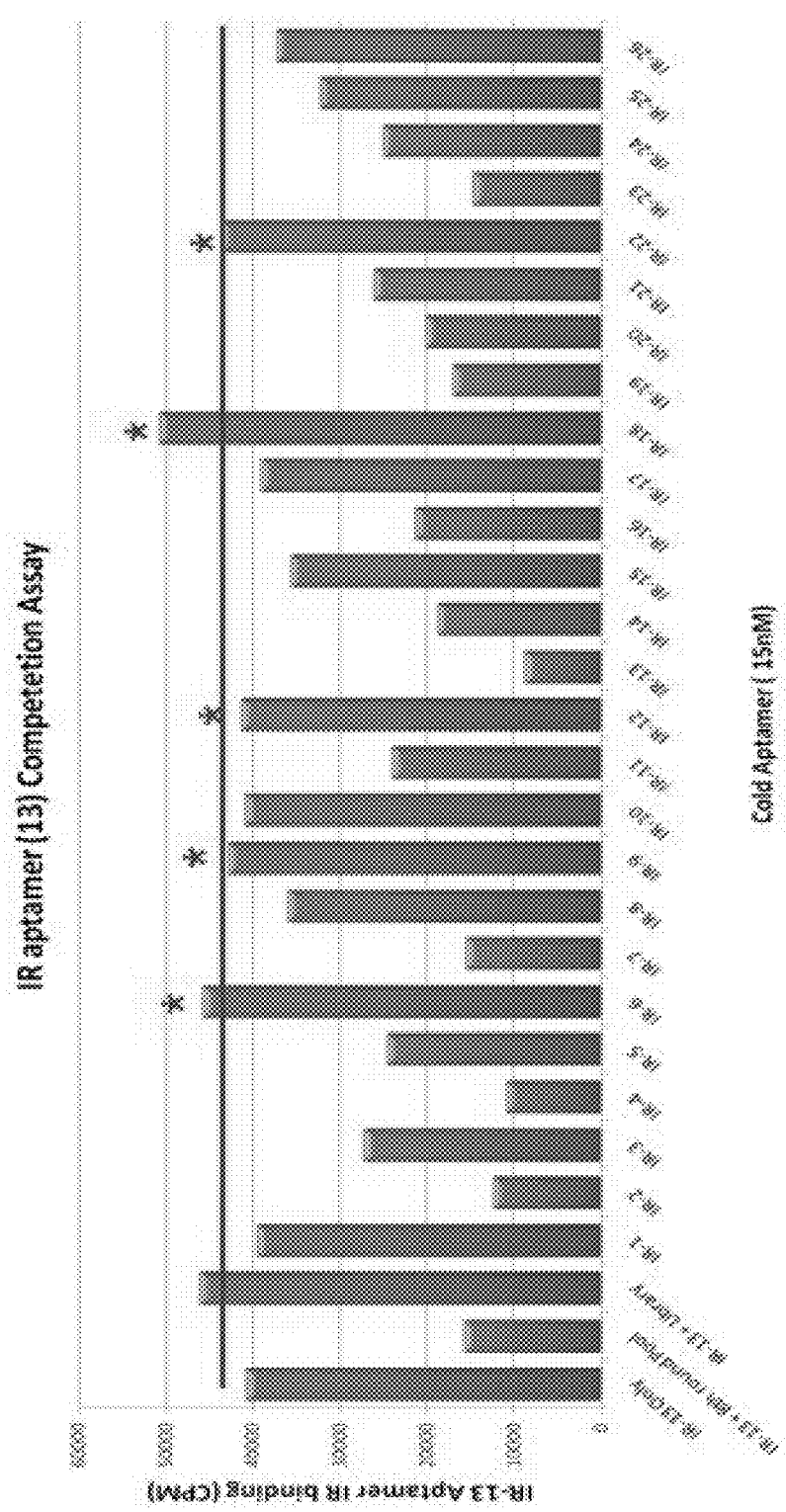
FIG. 4A is a bar graph showing the result of a competition assay for identifying the $2^{nd}$ aptamer of insulin receptor. As shown in the graph, the bound $^{32}$P-labeled IR-13 aptamer did not significantly compete out by IR-6, 9, 12, 18, and 22 aptamer clones.
Figure 4B:
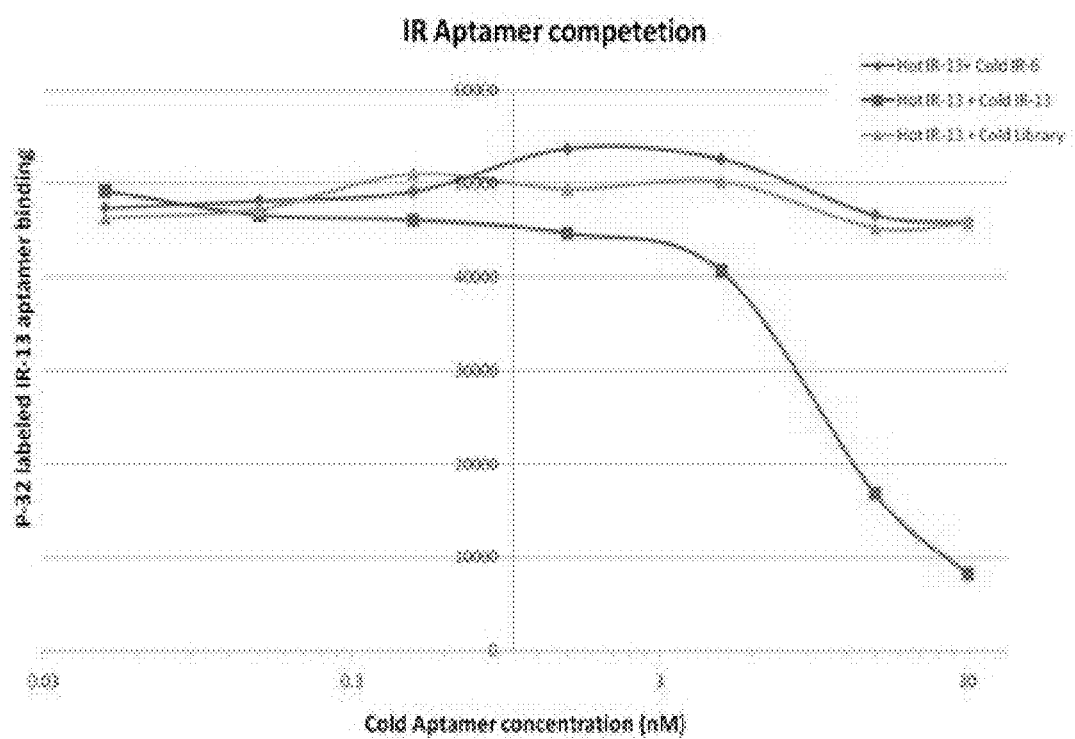
FIG. 4B is a graph showing the results of a competition assay at various concentrations. As can be seen, IR-6 aptamer did not significantly compete with $^{32}$P-labeled IR-13 (Hot IR-13). Unlabeled self IR-13 aptamer (Cold IR-13) was used as a control ('Hot' means $^{32}$P-labeled aptamers, and 'Cold' means the aptamers unlabeled).
Figure 5A:
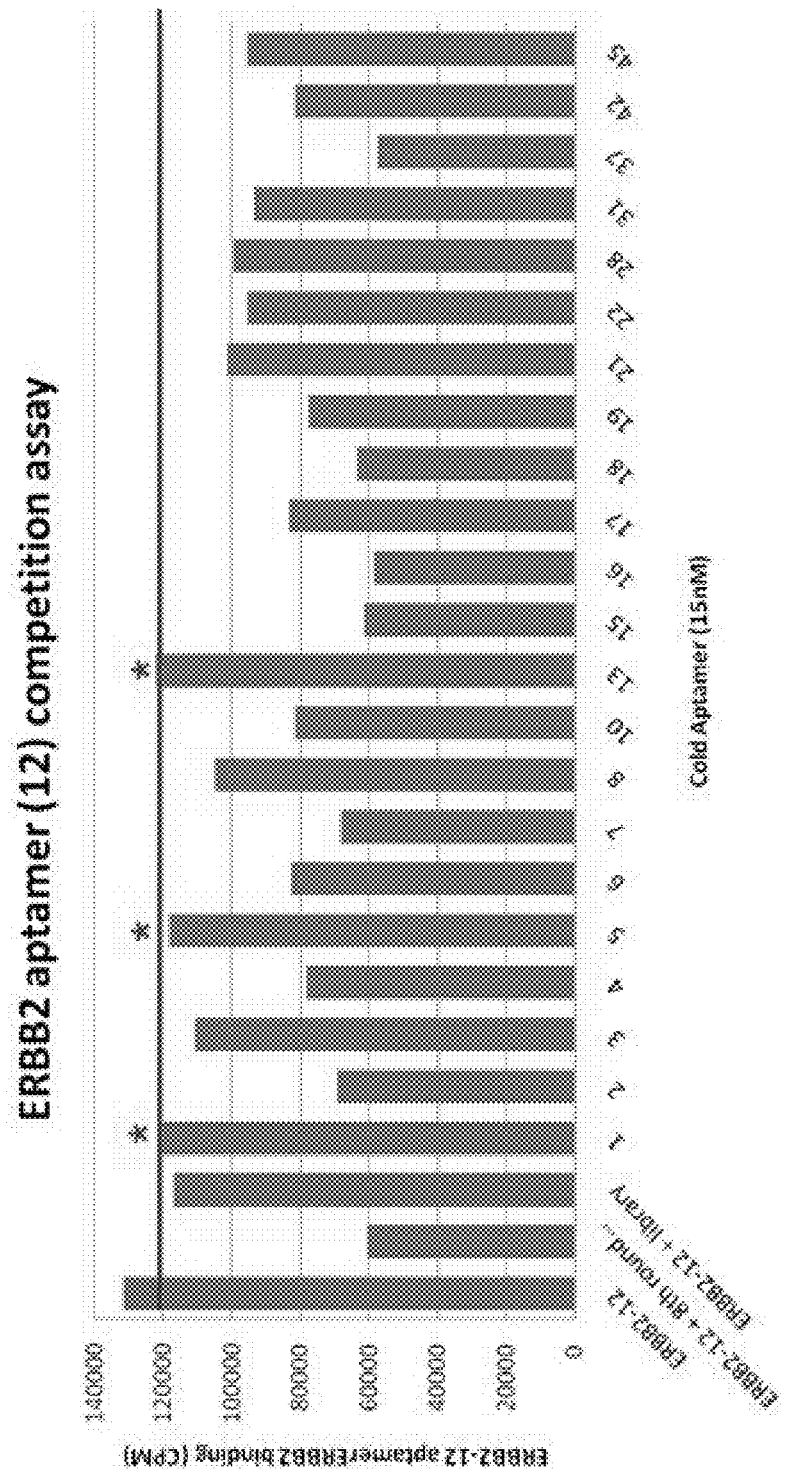
FIG. 5A is a graph showing the results of a competition assay in identifying the $2^{nd}$ aptamer of ERBB2. As shown in the graph, the bound $^{32}$P-labeled ERBB2-12 aptamer did not significantly compete out by ERBB2-1, 5 and 13 aptamer clones.
Figure 5B:
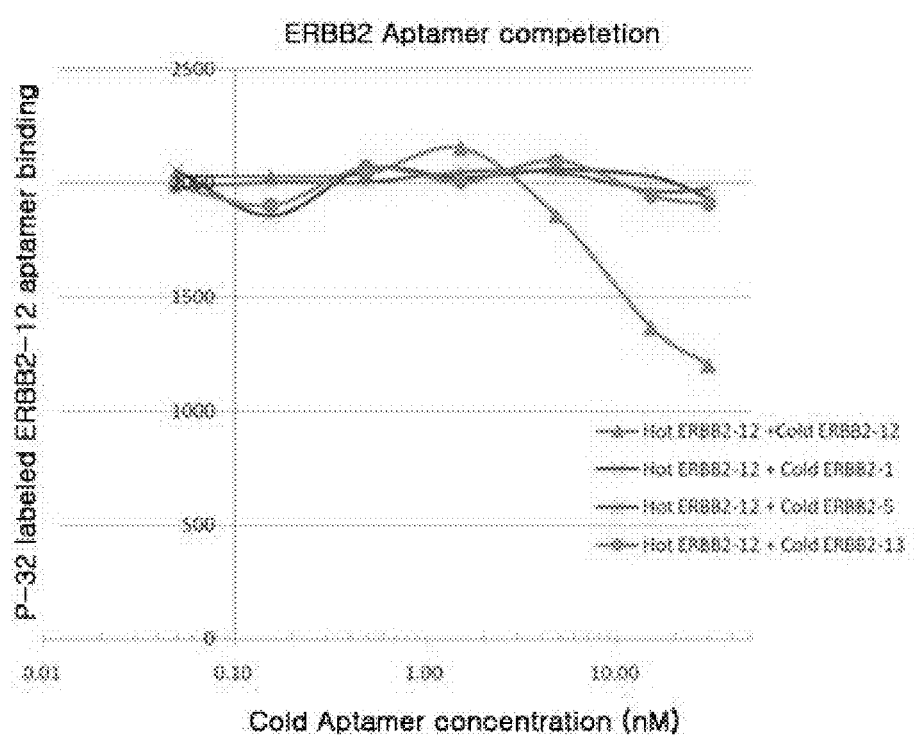
FIG. 5B is a graph showing the results of a competition assay at various concentrations. As can be seen, ERBB2-1, 5 and 13 aptamers did not compete significantly with $^{32}$P-labeled ERBB2-12 (Hot ERBB2-12). Unlabeled self ERBB2-12 aptamer (Cold ERBB2-12) was used as a control ('Hot' means $^{32}$P-labeled aptamers, and 'Cold' means the aptamers unlabeled).

Several aptamers were found not to bind competitively with the 1$^{st}$ binding aptamer. This non-competitive binding was confirmed in a wide range of second binding aptamer dose. As shown in FIGS. 4 and 5, the 2$^{nd}$ aptamer IR-6 (SEQ ID NO: 6) (Kd of 4.60 nM) did not bind competitively with IR-13 (SEQ ID NO: 13) and ERBB2-1 aptamer (SEQ ID NO: 27) (Kd of 3.05 nM) did not bind competitively with ERBB2-12 aptamer (SEQ ID NO: 33).

Example 4

Development of ELISA Assay with Two Aptamer Pairs and Comparison with Antibody-Based ELISA Assay 4.1. Aptamer-Based ELISA Assay To test the feasibility of using these aptamer pairs in ELISA assays, About 50 μL of 100 nM solution of an amine conjugated 1$^{st}$ target binding aptamers were linked to Anti-Amino ELISA plate (Nunc) for 2 hr at RT via a chemical cross-linking method and were used as capturing aptamers.

Figure 6:
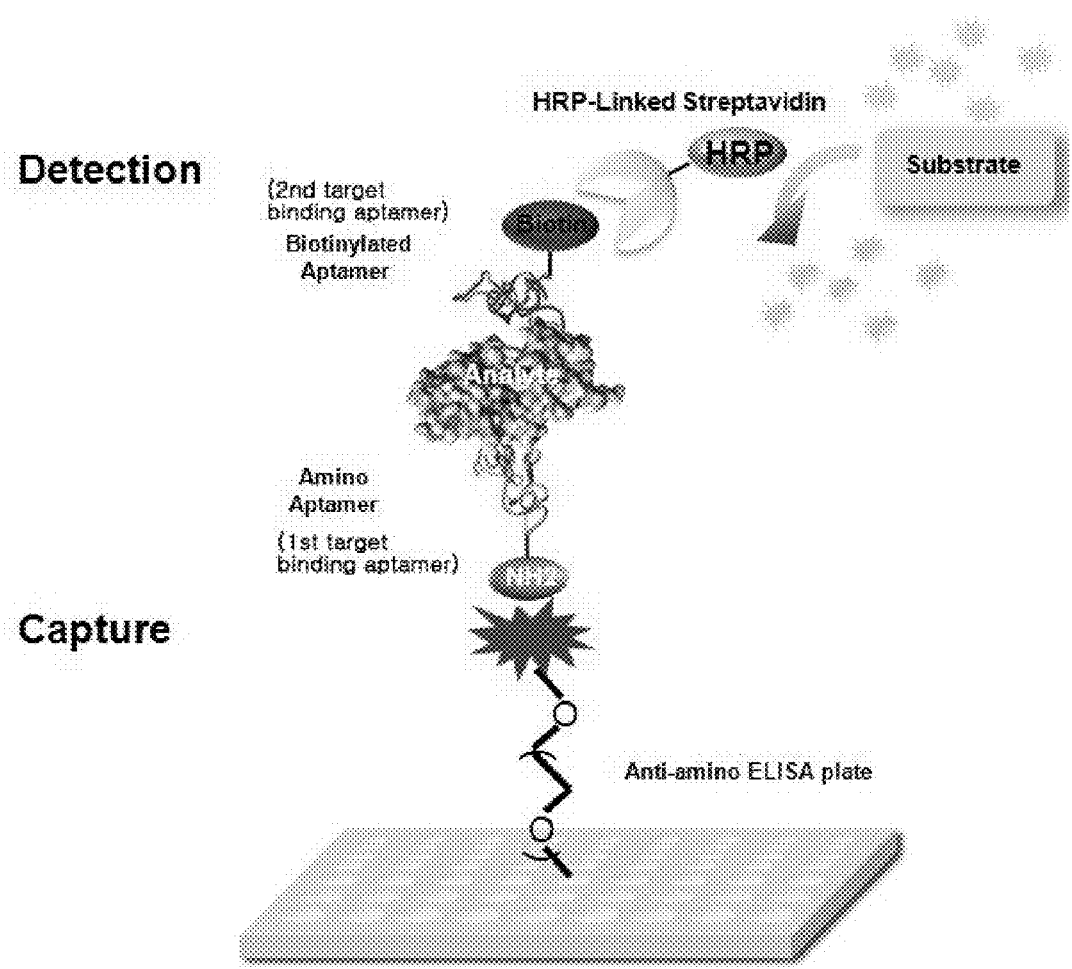
FIG. 6 is a schematic illustration of a sandwich assay. The capture aptamer synthesized with amine group at 5' terminus is immobilized on anti-amine capturing ELISA plate (ANTI-AMINO PLATE-NUNC). The coated aptamer is incubated with a sample. When present, the target protein and biotinylated detector aptamer form a sandwich on ELISA plate. HRP-conjugated streptavidin then binds to biotin and the resulting sandwiched complex is detected by an ELISA reader.

The plate was washed three times with Tris buffer containing 0.05% tween-20. The resulting conjugated complex was blocked with 1% BSA for 1 hr and with various concentrations of target proteins in 40 mM of HEPES/pH 7.5, 120 mM NaCl, 5 mM KCl, 5 mM MgCl2, 0.002% tween-20, and 0.1% BSA solution for 2 hr at RT. After washing three times with the buffer solution, the resulting plate was incubated with 100 μL, of 10 nM solution of biotinylated detection aptamer (second target binding aptamers) for 1 hr. The plate was then washed three times and incubated with 100 μL of 0.1 μg/ml of streptavidin conjugated HRP enzyme (RnD Systems) for 20 min at RT and biotin were detected using Horse radish peroxidase enzyme (HRP) conjugated streptavidin. See FIG. 6. The plate was washed three times and colored reaction of substrate was conducted. The reaction was stopped with 1 M of $H_2SO_4$ solution and the signal was detected with ELISA reader (Applied bioscience)

4.2. Comparison with Antibody-Based ELISA Assay

Commercial IR ELISA Kit (Human Total Insulin R DuoSet IC (Cat# DYC1544), RnD Systems) and ERBB2 ELISA Kit (Human Total Erbb2 DuoSet IC (Cat# DYC1129), RnD Systems) were used to compare the aptamer-based ELISA assay of example 4.1 with antibody-based ELISA assay.

Figure 7:
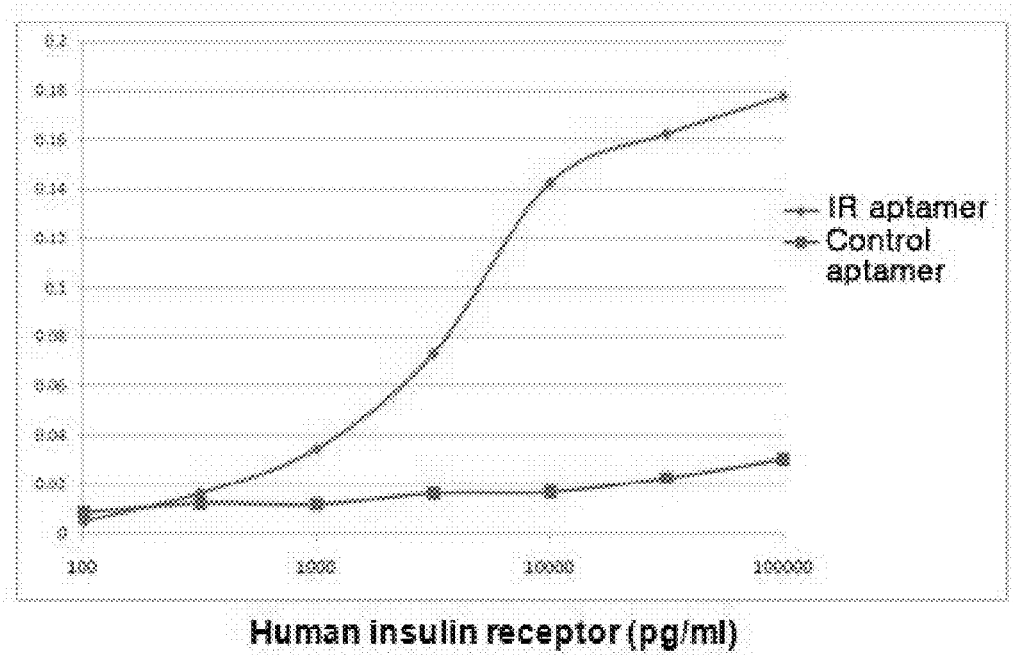
FIG. 7 shows a difference in sensitivity between an aptamer based ELISA assay of human insulin receptor using IR-13 aptamer as a capturing aptamer and biotinylated IR-6 aptamer as a detection aptamer and a commercially available antibody based IR detection ELISA assay.
Figure 7:
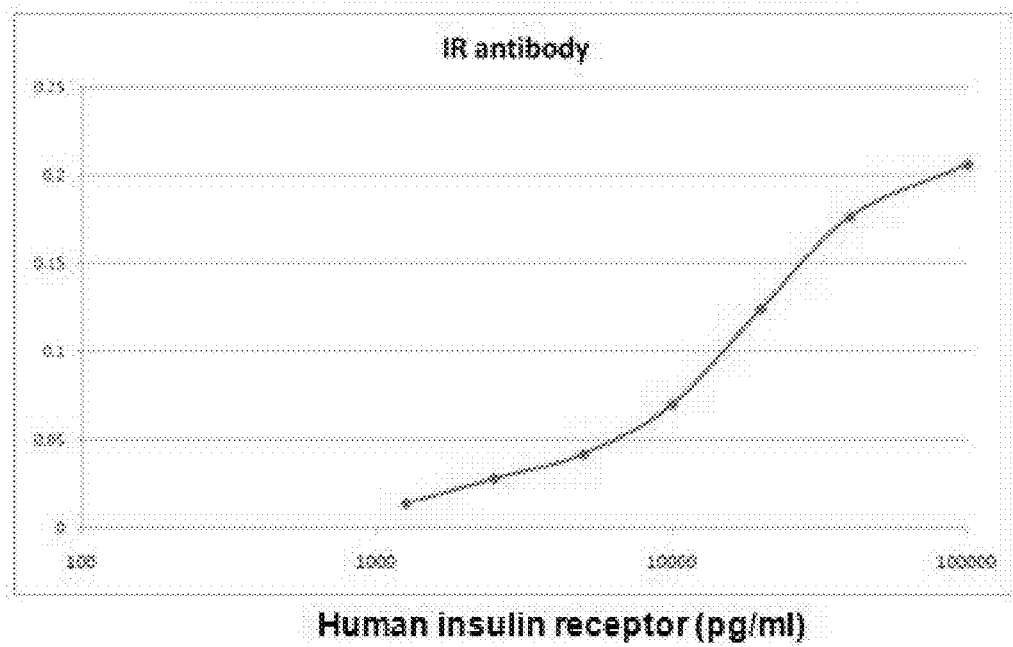
Figure 8:
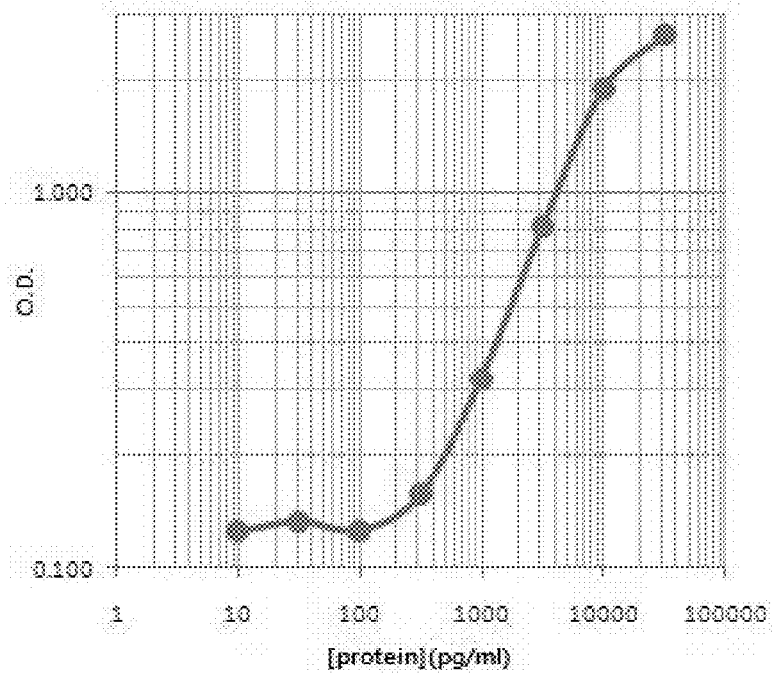
FIG. 8 shows a difference in sensitivity between an aptamer based ELISA assay of ERBB2 using ERBB2-12 aptamer as a capturing aptamer and biotinylated ERBB2-1 aptamer as a detection aptamer and a commercially available antibody based ERBB2 detection ELISA assay.
Figure 8:
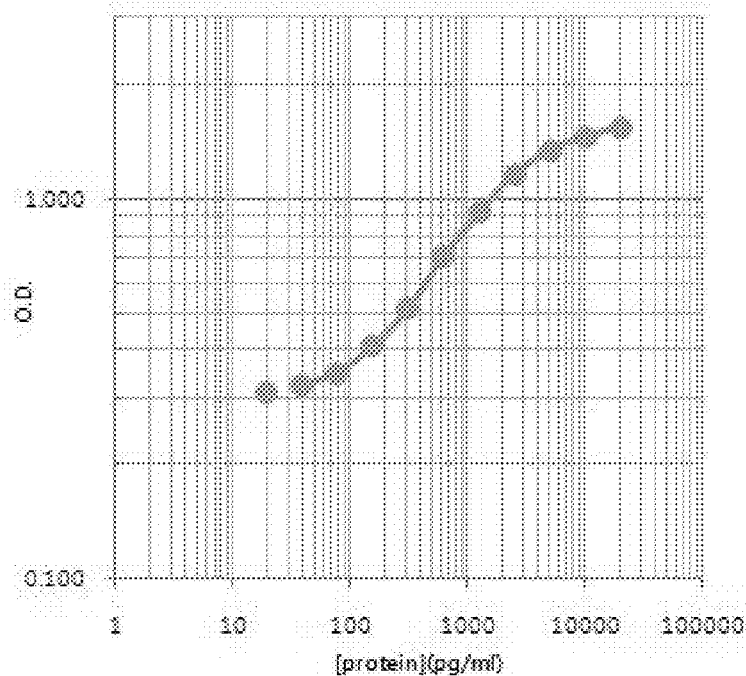

It was found that ELISA assay using aptamer pairs can detect ERBB2 and IR with better performance than antibody-based ELISA assay. IR-aptamer assay shows 10 times better sensitivity (detects from 316 pg/mL) than commercial IR kit does (detects from 3.16 ng/mL). Although ERBB2-aptamer assay shows similar sensitivity (200 pg/mL) with ERBB2 ELISA Kit, ERBB2-aptamer assay shows 2 times lower background signal (<0.150 OD) than commercial ERBB2 ELISA kit does (>0.300 OD). These results show that aptamer pairs founded from the same SELEX process can be used as competitive tool in sandwich assays with many benefits. See FIGS. 7 and 8.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for identifying a pair of aptamers that binds to separate non-overlapping sites on a target molecule, the method comprising:
(a) preparing a plurality of candidate aptamers having a binding affinity to the target molecule by synthesizing an oligonucleotide library comprising a plurality of oligonucleotides that consist of random nucleotide sequences having lengths of 35-45 nucleotides flanked by two fixed nucleotide sequences having lengths of 15-25 nucleotides, one of the two fixed nucleotide sequences being located at a 4'-end and the other one of the two fixed nucleotide sequences being located at a 3'-end, and by selecting the plurality of candidate aptamers from the oligonucleotide library using a SELEX (systematic evolution of ligands by exponential enrichment) process;

(b) selecting a first aptamer having a dissociation constant (Kd) of 10 nM or less from the plurality of candidate aptamers by measuring the dissociation constants of the plurality of candidate aptamers binding to the target molecule under conditions of 35-40° C. and pH 7.0-8.0 and determining candidate aptamers having a Kd of 10 nM or less as the first aptamer;

(c) selecting a second aptamer from the plurality of candidate aptamers, wherein the second aptamer has a dissociation constant of 100 nM or less and is capable of binding to a non-overlapping site of the target molecule, and wherein the second aptamer is determined by labeling the first aptamer with a detectable label, forming a complex of the labeled first aptamer and the target molecule;

(d) contacting the complex with the plurality of candidate aptamers, and detecting candidate aptamers having non-competitive binding affinity to the complex.

2. The method of claim 1, wherein the non-competitive binding of the candidate aptamers is detected by measuring a fraction of the candidate aptamers bound to the complex at a-various concentrations of the candidate aptamers.

3. The method of claim 1, wherein the target molecule is insulin receptor.

4. The method of claim 1, wherein the random nucleotide sequences of the plurality of candidate aptamers comprises a nucleic acid sequence selected from the group consisting of SEQ ID NOS: 1-26.

5. The method of claim 1, wherein the target molecule is ERBB2.

6. The method of claim 1, wherein the random nucleotide sequences of the plurality of candidate aptamers comprises a nucleic acid sequence selected from the group consisting of SEQ ID NOS: 27-57.

7. The method of claim 1, wherein the first aptamer is labeled by an optical label, a radio label, an isotope label, or a combination thereof.

8. The method of claim 7, wherein the optical label is fluorophore selected from fluorescein, rhodamine, cyanine, eosin, coumarin, TEXAS RED, ALEXA, CF dyes, Fluoprobes, DYLIGHT fluors, OYSTER dyes, ATTO dyes, and HILIGHT FLUORES.

9. The method of claim 1, further comprising amplifying the plurality of candidate aptamers prior to selecting the first aptamer.

10. The method of claim 9, wherein the amplification of the SELEX process is performed by using a nucleic acid polymerase is-selected from the group consisting of DNA polymerase, RNA polymerase, reverse transcriptase, and Qβ-replicase.

11. A method for detecting a target molecule in a sample by performing a sandwich assay using the pair of aptamers identified according to the method of claim 1, the method comprising:

immobilizing the first aptamer on a solid substrate;

treating the first aptamer immobilized on the solid substrate with the sample and then contacting with the second aptamer labeled with a detectable label to form a sandwich complex of the second aptamer, the target molecule, and the first aptamer immobilized on the solid substrate; and at least detecting the presence of the target molecule in the sample by detecting the detectable label of the complex or by measuring the quantity of the target molecule in the sample.

12. The method of claim 11, wherein the target molecule is protein, peptide, oligosaccharide, oligonucleotide, hemoglobin, phospholipid, glycolipid, sterol, glycerolipids, carbohydrates, sugar, vitamins, hormones, neurotransmitters, or metabolites.

13. The method of claim 11, wherein the protein is selected from the group consisting of insulin receptor, ERBB2, E2, and a combination thereof.

14. The method of claim 11, wherein the sample is a biological fluid selected from the group consisting of blood, plasma, serum, sputum, urine, semen, cerebrospinal fluid, bronchial aspirate, macerated tissue, and rheumatoid arthritis fluid, or a mixture thereof.

15. The method of claim 11, wherein the detectable label is selected from the group consisting of fluorophore, radio isotope, enzyme, fluorescence polarization, surface plasmon resonance, diffractive optics technology, biolayer interferometry, colorimetric resonant reflection, resonant waveguide grating, and a combination thereof.

16. The method of claim 15, wherein the fluorophore is selected from the group consisting of fluorescein, rhodamine, cyanine, eosin, coumarin, TEXAS RED, ALEXA, CF dyes, FLUOPROBES, DYLIGHT fluors, OYSTER dyes, ATTO dyes, and HILIGHT FLUORES.

17. The method of claim 12, wherein the solid substrate is selected from the group consisting of a microsphere particle, glass, a silicon wafer, a membrane, a metal, a polymer, and a combination thereof.

* * * * *

UNITED STATES PATENT AND TRADEMARK OFFICE
CERTIFICATE OF CORRECTION

PATENT NO. : 8,785,132 B2  
APPLICATION NO. : 13/092209  
DATED : July 22, 2014  
INVENTOR(S) : Young-Chan Chae et al.

Page 1 of 1

It is certified that error appears in the above-identified patent and that said Letters Patent is hereby corrected as shown below:

On the Title Page, item 73, in the Assignee of the patent, delete "Phang-Shi (KR)" and insert --Pohang-Shi (KR)--.

On the Title Page, item 73, in the Assignee of the patent, after "Postech Academy-Industry Foundation, Pohang-Shi (KR)", insert --POSCO, Pohang-shi (KR)--.

Signed and Sealed this  
Nineteenth Day of May, 2015

Michelle K. Lee  
*Director of the United States Patent and Trademark Office*

SEQUENCE LISTING

<160> NUMBER OF SEQ ID NOS: 60

<210> SEQ ID NO 1
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 1
aagggtaggc atatatctcg aggtcggagt aaccgcttga                           40

<210> SEQ ID NO 2
<211> LENGTH: 40
<212> TYPE: DNA
<213> ORGANISM: Artificial Sequence

```
<220> FEATURE:
<223> OTHER INFORMATION: random nucleotide of insulin receptor aptamer

<400> SEQUENCE: 2
gcatgcttct taggcctgat ggccgaccag tttgacggaa                              40

<210> SEQ ID NO 3
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 3
agtgattcaa attatgaccc cctttttaaag agcatacaaa                             40

<210> SEQ ID NO 4
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 4
attattaacg agatgcatca tgcctgatac cagactaagc                              40

<210> SEQ ID NO 5
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 5
ggttcgtgac tgaactcggt gtgggtggct tgggtttggt                              40

<210> SEQ ID NO 6
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 6
tgggtacagt ctttagctta cacaggctcc tgaagacgca                              40

<210> SEQ ID NO 7
<211> LENGTH: 39
<212> TYPE: DNA
<213> ORGANISM: Artificial Sequence
<220> FEATURE:
<223> OTHER INFORMATION: random nucleotide of insulin receptor aptamer

<400> SEQUENCE: 7
ttgattatta acgagatgag ccctcctga caacctcac                                39

<210> SEQ ID NO 8
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 8
tgtatgagct gatgcggttt caccgagcag acagactcct                              40
```

<210> SEQ ID NO 9
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 9
agatcggtgc caagtctccc ttttctggtc cgctgataga        40

<210> SEQ ID NO 10
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 10
tgtggtgtaa ctattattaa tgagatgcag taggcctgac        40

<210> SEQ ID NO 11
<211> LENGTH: 39
<212> TYPE: DNA
<213> ORGANISM: Artificial Sequence
<220> FEATURE:
<223> OTHER INFORMATION: random nucleotide of insulin receptor aptamer

<400> SEQUENCE: 11
taaggtttaa gcttggccta atggtgctat caggctcag        39

<210> SEQ ID NO 12
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 12
tgggtacagt gtttagcttg cacaggctcc tgaagacact        40

<210> SEQ ID NO 13
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 13
ttatccacta tggcttctca ttcaaataag tgcgatcgat        40

<210> SEQ ID NO 14
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 14
gcatgcttct taggactgat ggccgaccag tctgacggaa        40

<210> SEQ ID NO 15
<211> LENGTH: 40
<212> TYPE: DNA
<213> ORGANISM: Artificial Sequence
<220> FEATURE:
<223> OTHER INFORMATION: random nucleotide of insulin receptor aptamer

```
<400> SEQUENCE: 15
aggaacttgc ccgttgctgt ttcattagct gatgcgctta                           40

<210> SEQ ID NO 16
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 16
gaatgtcgcc ctttctcatt gaaattatgg cgtggaggta                           40

<210> SEQ ID NO 17
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 17
gtcgcctgat ggcggtggct ttatgcttta aagtcacggg                           40

<210> SEQ ID NO 18
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 18
gcctgacctc attcacgcac tgttgggcag actatgaatt                           40

<210> SEQ ID NO 19
<211> LENGTH: 39
<212> TYPE: DNA
<213> ORGANISM: Artificial Sequence
<220> FEATURE:
<223> OTHER INFORMATION: random nucleotide of insulin receptor aptamer

<400> SEQUENCE: 19
ggtcgtgact gaactcggtg tgggtggctt gggtttgtt                            39

<210> SEQ ID NO 20
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 20
aaagcagtgc atggctattt attaagaaag acgggagttt                           40

<210> SEQ ID NO 21
<211> LENGTH: 39
<212> TYPE: DNA
<213> ORGANISM: Artificial Sequence
<220> FEATURE:
<223> OTHER INFORMATION: random nucleotide of insulin receptor aptamer

<400> SEQUENCE: 21
agttgccgcc gtcttcattg aactgtacta ggtgccctc                            39

<210> SEQ ID NO 22
```

```
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 22
ataaaccatt ccgtggctgg ctgacctctt tcacgcgatc                              40

<210> SEQ ID NO 23
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 23
tgtgattcaa attatggccc cctttaaag agcatacaaa                               40

<210> SEQ ID NO 24
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 24
ggactcttac gcggttaacc ctcatggttt tgtgagtctg                              40

<210> SEQ ID NO 25
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 25
agatccgact gtttactgtt taacagccgg ctgatggacc                              40

<210> SEQ ID NO 26
<211> LENGTH: 40
<212> TYPE: DNA
<213> ORGANISM: Artificial Sequence
<220> FEATURE:
<223> OTHER INFORMATION: random nucleotide of insulin receptor aptamer

<400> SEQUENCE: 26
tgtataattg ggttcttgaa attaccccga agctaggtca                              40

<210> SEQ ID NO 27
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 27
atgttagagt ttgcctgagt gcctcgtaag ggcgtaacaa                              40

<210> SEQ ID NO 28
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 28
```
tactgggccc gttagcctct ggcgctcctt cgcttgtgcc                         40

<210> SEQ ID NO 29
<211> LENGTH: 36
<212> TYPE: DNA
<213> ORGANISM: Artificial Sequence
<220> FEATURE:
<223> OTHER INFORMATION: random nucleotide of ERBB2 aptamer

<400> SEQUENCE: 29
ttatcaacgc actgagggcg tcagcttctt tttagg                             36

<210> SEQ ID NO 30
<211> LENGTH: 39
<212> TYPE: DNA
<213> ORGANISM: Artificial Sequence
<220> FEATURE:
<223> OTHER INFORMATION: random nucleotide of ERBB2 aptamer

<400> SEQUENCE: 30
atgtagagtt tgcctgagtg cctcgcaagg gcgtaacag                          39

<210> SEQ ID NO 31
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 31
tcctgtcccg gtttacacaa gttaaggcag ccgctggata                         40

<210> SEQ ID NO 32
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 32
gtctgaacac cgagattagc tgaacgaacg gtatggacgt                         40

<210> SEQ ID NO 33
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 33
tcctggcatg ttcgatggag gcctttgatt acagcccaga                         40

<210> SEQ ID NO 34
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 34
cgcgattaga tgaacgcaca atacccgttc tgagtaaagt                         40

<210> SEQ ID NO 35
<211> LENGTH: 40
<212> TYPE: DNA

<213> ORGANISM: Artificial Sequence
<220> FEATURE:
<223> OTHER INFORMATION: random nucleotide of ERBB2 aptamer

<400> SEQUENCE: 35
gtctgaacac cgagattagc cgaacgaacg gtatggacgt                    40

<210> SEQ ID NO 36
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 36
gttagactga acgcactgag ggccgcagcc tatctgaagg                    40

<210> SEQ ID NO 37
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 37
atgttagagt ttgcctgagt gcctcgcaag ggcgtaacaa                    40

<210> SEQ ID NO 38
<211> LENGTH: 41
<212> TYPE: DNA
<213> ORGANISM: Artificial Sequence
<220> FEATURE:
<223> OTHER INFORMATION: random nucleotide of ERBB2 aptamer

<400> SEQUENCE: 38
gtctgagcat cgcgtttagc cgaacgctcg gtgaggtaga t                  41

<210> SEQ ID NO 39
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 39
tcatggcatg ttcgatggag gcctttgatt acagcccaga                    40

<210> SEQ ID NO 40
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 40
ctacacgaat caactcccct ccgcatactg aacatcacaa                    40

<210> SEQ ID NO 41
<211> LENGTH: 39
<212> TYPE: DNA
<213> ORGANISM: Artificial Sequence
<220> FEATURE:
<223> OTHER INFORMATION: random nucleotide of ERBB2 aptamer

<400> SEQUENCE: 41
ttagcaaaat gccatgtgcg tcctgtcccg gtttacagc                     39

<210> SEQ ID NO 42
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 42
tgatgtcccc aactcagctg tgaatctatg cccccgccca                40

<210> SEQ ID NO 43
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 43
ctgagcggtt actacaccac cgtgagacct tagttacaaa                40

<210> SEQ ID NO 44
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 44
attagatgaa agcgcattcc aacaacagat aatctgaggg                40

<210> SEQ ID NO 45
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 45
tttggagtgt cttacggttg gagtaatcga ggatggatga                40

<210> SEQ ID NO 46
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 46
ccgttaccta cctcctcgac cgtgggtgcc cttagtccca                40

<210> SEQ ID NO 47
<211> LENGTH: 39
<212> TYPE: DNA
<213> ORGANISM: Artificial Sequence
<220> FEATURE:
<223> OTHER INFORMATION: random nucleotide of ERBB2 aptamer

<400> SEQUENCE: 47
tcctggcatg ttcgatggag gcctttgatt acagccaga                39

<210> SEQ ID NO 48
<211> LENGTH: 40
<212> TYPE: DNA
<213> ORGANISM: Artificial Sequence
<220> FEATURE:

<223> OTHER INFORMATION: random nucleotide of ERBB2 aptamer

<400> SEQUENCE: 48
ccgttaccta cctcctcgac cgtgggtgcc tttagtccca                                40

<210> SEQ ID NO 49
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 49
tcctggcatg ttcgatggag gcctttgatt acagcccagt                                40

<210> SEQ ID NO 50
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 50
attagatgaa agcacattcc aacaacagat aatctgaggg                                40

<210> SEQ ID NO 51
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 51
atgttagagt ttgcctgagt gcgtcgcaag ggcgtaacag                                40

<210> SEQ ID NO 52
<211> LENGTH: 39
<212> TYPE: DNA
<213> ORGANISM: Artificial Sequence
<220> FEATURE:
<223> OTHER INFORMATION: random nucleotide of ERBB2 aptamer

<400> SEQUENCE: 52
tgagaagggc tgtgccttac tcaaaatttg ggatctgaa                                 39

<210> SEQ ID NO 53
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 53
tcctggtatg ttcgatggag gcctttgatt acagcccaga                                40

<210> SEQ ID NO 54
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 54
tagatctctg attaggtaga acgccctact ctaacggcag                                40

```
<210> SEQ ID NO 55
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 55
tgagaagggc tgtgccttac tcaaaatttg gggatctgaa                             40

<210> SEQ ID NO 56
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 56
cgtccttggt gagtttgggt ctgagcagga gcacgtgagt                             40

<210> SEQ ID NO 57
<211> LENGTH: 40
<212> TYPE: DNA
<213> ORGANISM: Artificial Sequence
<220> FEATURE:
<223> OTHER INFORMATION: random nucleotide of ERBB2 aptamer

<400> SEQUENCE: 57
atgttagagt ctgcctgagt gcctcgcaag ggcgtaacag                             40

<210> SEQ ID NO 58
<211> LENGTH: 17
<212> TYPE: DNA
<213> ORGANISM: Artificial Sequence
<220> FEATURE:
<223> OTHER INFORMATION: fixed nucleotide of aptamer at 5' end, and also
      a forward primer to amplify the aptamer

<400> SEQUENCE: 58
gagtgaccgt ctgcctg                                                      17

<210> SEQ ID NO 59
<211> LENGTH: 17
<212> TYPE: DNA
<213> ORGANISM: Artificial Sequence
<220> FEATURE:
<223> OTHER INFORMATION: fixed nucleotide of aptamer at 3' end

<400> SEQUENCE: 59
cagccacacc accagcc                                                      17

<210> SEQ ID NO 60
<211> LENGTH: 17
<212> TYPE: DNA
<213> ORGANISM: Artificial Sequence
<220> FEATURE:
<223> OTHER INFORMATION: reverse primer

<400> SEQUENCE: 60
ggctggtggt gtggctg                                                      17
```